(12) United States Patent
Vakhshoori et al.

(10) Patent No.: US 10,067,055 B1
(45) Date of Patent: Sep. 4, 2018

(54) DEVICES AND METHODS FOR COHERENT DETECTION USING CHIRPED LASER PULSES

(71) Applicant: Pendar Technologies, LLC, Cambridge, MA (US)

(72) Inventors: Daryoosh Vakhshoori, Cambridge, MA (US); Romain Blanchard, Lexington, MA (US); Tobias Mansuripur, Somerville, MA (US)

(73) Assignee: PENDAR TECHNOLOGIES, LLC, Cambridge, MA (US)

( * ) Notice: Subject to any disclaimer, the term of this patent is extended or adjusted under 35 U.S.C. 154(b) by 0 days.

(21) Appl. No.: 15/593,248

(22) Filed: May 11, 2017

Related U.S. Application Data

(60) Provisional application No. 62/468,541, filed on Mar. 8, 2017, provisional application No. 62/334,789, filed on May 11, 2016.

(51) Int. Cl.
  *G01N 21/00* (2006.01)
  *G01N 21/45* (2006.01)

(52) U.S. Cl.
  CPC ....... *G01N 21/45* (2013.01); *G01N 2021/451* (2013.01); *G01N 2201/06113* (2013.01)

(58) Field of Classification Search
  CPC ............. G01N 21/45; G01N 2021/451; G01N 2201/06113
  USPC .......................................................... 356/72
  See application file for complete search history.

(56) References Cited

U.S. PATENT DOCUMENTS

| 7,826,509 B2 | 11/2010 | Belkin et al. | |
| 9,246,310 B2 | 1/2016 | Goyal et al. | |
| 2006/0244973 A1* | 11/2006 | Yun ...................... | A61B 5/0059 356/511 |
| 2015/0014543 A1* | 1/2015 | Weidmann .............. | G01S 17/32 250/349 |

OTHER PUBLICATIONS

Nikodem et al. ("Chirped Laser Dispersion Spectroscopy for Remote Open-Path Trace-Gas Sensing", Sensors 2012, 12, pp. 16466-16481).*
Coddington et al., "Dual-comb spectroscopy," Optica, vol. 3, pp. 414-426 (Apr. 2016).

(Continued)

*Primary Examiner* — Hina F Ayub
(74) *Attorney, Agent, or Firm* — Smith Baluch LLP

(57) ABSTRACT

We present here systems and methods for generating a heterodyne signal using the naturally occurring chirp of a pulsed single-mode laser. The electrical square-wave pulse used to drive the laser heats the laser cavity, causing the laser frequency to change or chirp during the emission of the optical pulse. This chirped optical pulse can be split into a chirped signal pulse that interacts with a sample and a chirped reference pulse that interferes with the chirped signal pulse on a detector to produce a heterodyne modulation whose instantaneous phase and amplitude depend on the sample's dispersion and absorption, respectively. The chirp is reproducible, so the heterodyne modulation, instantaneous phase, and/or instantaneous amplitude can be average over many measurements, either with multiple pulses from the same laser or multiple pulses from different lasers, each emitting at a different wavelength.

24 Claims, 19 Drawing Sheets

$$S = I_R(t) + I_s(t) + 2\sqrt{I_R(t)I_s(t)}\cos(\Delta f(t).t + \varphi)$$

$$\frac{S - I_R(t)}{2\sqrt{I_R(t)}} \sim \sqrt{I_s(t)}\cos(\Delta f(t).t + \varphi)$$

(56) References Cited

OTHER PUBLICATIONS

Ezra Ip et al., "Coherent detection in optical fiber systems," Opt. Express 16, pp. 753-791 (2008).
Lee et al., "Widely tunable single-mode quantum cascade laser source for mid-infrared spectroscopy," Appl. Phys. Lett. 91, 231101 (2007).
Nesci et al., "Quantitative amplitude and phase measurement by use of a heterodyne scanning near-field optical microscope," Opt. Lett. 26, pp. 208-210 (2001).
Nikodem et al., "Chirped laser dispersion spectroscopy with harmonic detection of molecular spectra," Appl. Phys. B 109, pp. 477-483 (2012).
Nikodem et al., "Chirped lasers dispersion spectroscopy implemented with single- and dual-sideband electro-optical modulators," Opt. Express 21, pp. 14649-14655 (Jun. 17, 2013).

* cited by examiner

Figure 9A Without vibration

Figure 9B With vibration

US 10,067,055 B1

DEVICES AND METHODS FOR COHERENT DETECTION USING CHIRPED LASER PULSES

CROSS-REFERENCE TO RELATED APPLICATIONS

This application claims the priority benefit, under 35 U.S.C. § 119(e), of U.S. Application No. 62/468,541, filed Mar. 8, 2017, and of U.S. Application No. 62/334,789, filed May 11, 2016. Each of these applications is incorporated herein by reference for all purposes in its entirety.

BACKGROUND

Coherent detection is a well-established technique in telecommunication and spectroscopy. It refers to the detection of the interference between a reference signal (often referred to as a 'local oscillator') having a large power (compared to the noise level of the detector) and a weak measurement signal, as a way to extract the information (power) of the weak signal. The interference signal is modulated at the difference frequency between the local oscillator and the weak signal.

Coherent amplification results when a signal interferes with a local oscillator to produce a heterodyne coherent beat on a detector:

$$P(t)_{Coherent,i} = P(t)_{ref,i} + P(t)_{s,i} + 2\sqrt{P(t)_{ref,i} \cdot P(t)_{s,i}} \cos[(\omega_{ref,i} - \omega_{s,i})t]$$

where $P(t)_{Coherent,i}$ is the coherent power interference on detector, $P(t)_{ref,i}$ is the reference pulse power, $P(t)_{s,i}$ is the signal pulse power, $\omega_{ref,i}$ is the reference frequency, and $\omega_{s,i}$ is the signal frequency. Typically, the frequency of reference and signal are fixed resulting in a constant difference frequency beat in the detector. For homodyne detection, the difference frequency $\Delta\omega = (\omega_{ref} - \omega_s)$ is nominally zero and the information is coded either in the phase difference between signal and reference or in a frequency shift of the signal. For heterodyne detection, the difference frequency is not nominally zero. The beat frequency is the modulation frequency $\Delta\omega$ of the heterodyne signal. When the beat frequency is constant, its intensity can be extracted by using a band-pass filter centered at $\Delta\omega$, lock-in amplification, or using other signal recovery methods.

Both reference and signal can be derived from a single laser source. A heterodyne signal can be generated if a phase-modulation or frequency shift is provided to either reference or signal. For example, a frequency-shifted reference signal can be obtained from a single laser source using an acousto-optic modulator (AOM). Alternatively, phase-modulation can be realized by electro-optic modulators (EOM) or piezo-electric phase modulators. Coherent detection by phase-modulation is known as pseudo-heterodyne detection.

In optical double-comb spectroscopy, the difference frequency is not zero and each wavelength channel used for spectroscopy has a unique (multiple of a known base) difference frequency. The amplitude of each beat difference frequency is measured (in the RF domain) and is assigned to the spectrum sample centered at the corresponding frequency of the signal laser. Implementation of sources for a double-comb spectroscopy is however difficult.

SUMMARY

We present here systems and methods for generating a heterodyne signal using the naturally occurring chirp of a pulsed single-mode laser. A heterodyne signal is generated by making use of a chirped laser source (i.e., a laser whose emission frequency changes with time) due to heating of the laser cavity by the electrical pulse used to drive the laser. The chirped pulse emitted by the laser can be split into reference and signal portions (using, for example, a beam splitter). Delaying the reference portion with respect to the signal portion or vice versa, e.g., with different optical path lengths for the reference and signal channels, yields a frequency difference when the reference and signal portions interfere with each other. Note that no frequency-shift or phase-modulation device is needed. Instead, the laser chirps naturally (due, for example, to heating of the active region during the duration of the electrical driving pulse), and the effective time delay between signal and reference generates a heterodyne modulation of the measured intensity. In some cases, the laser chirp is nonlinear, so the instantaneous frequency of the heterodyne modulation varies with time (and with the relative time delay).

The time delay can be introduced either by having different geometric lengths between the reference and signal paths, by dispersive effects along one or both paths, or both. Note that dispersive effects can be due, for example, to the presence of an absorbing material along one or both paths.

If a chirped pulse interrogates a substance and the resultant signal pulse is collected and interfered on a detector with a local reference pulse (tap from the same pulse), there will be a heterodyne modulation (ripple) riding on top of the detected pulse waveform. The magnitude of this heterodyne modulation is proportional to the square root of the signal intensity and the frequency of the modulation is related to the time delay between the signal and the local reference pulse. We call this Chirp-Delay Heterodyne measurement. If multiple lasers each at different wavelengths are used to spectroscopically or analytically interrogate a substance or a property of an object, we call this technique Chirp-Delay Heterodyne Spectroscopy.

If the reference optical pulse is a second (distinct) pulse from a train of pulses, interference would occur and could still be electronically detected as long as the frequency separation of the two pulses is within the detection frequency bandwidth. We call this technique Double-Pulse Chirp-Delay Heterodyne measurement and correspondingly Double-Pulse Chirp-Delay Heterodyne Spectroscopy for measurements made with multiple lasers.

We also present here systems and methods for detecting the phase and dispersion of a sample using the heterodyne signal generated by Chirp Delay Heterodyne Spectroscopy (CDHS). Data collected by CDHS yields information about the phase and dispersion of the sample. This information is complementary to the absorption information that is also present in the collected CDHS signal. By allowing retrieval of the dispersion signature associated with a sharp absorption line, CDHS provides a mechanism for a baseline free measurement and a quantitative measurement (e.g., measurement of an analyte concentration) independent of laser pulse intensity.

If a chirped pulse is sent out to interrogate a substance and the resultant signal pulse is collected and interfered on a detector with a local reference pulse (tap from the same pulse), there would be a modulation (ripple) riding on top of the detected pulse waveform. The magnitude of this modulation is proportional to the square root of the signal and the frequency of the modulation is related to the time delay between the signal and the local reference pulse. The phase of the modulation is related to the dispersion in the signal path (in addition to the time delay between the signal and local reference pulse.)

Chirp delay heterodyne spectroscopy provides signal gain. Examples of experimental situations in which low signal-to-noise ratios (SNRs) can be encountered include but are not limited to: transmission spectroscopy through optical thick samples (e.g., liquid cell with aqueous solvent); stand-off measurement using scattering off a rough surface to generate a diffuse reflected signal (only a small portion of which is collected by the receiving optics); measurements using uncooled detectors with lower detectivity than cooled detectors (a choice that can be driven by a desire to reduce the size, weight or power consumption of the instrument); and long distance, open-path, transmission spectroscopy, where the aperture of the receiving telescope limits the amount of signal collected. The techniques described here enable coherent gain of the signal using a single source, no moving parts, no modulator, and no active phase locking.

Advantages of the techniques presented here include: simplicity, by providing a low size, weight and power solution to obtain coherent gain, with no moving parts, no external modulator; stability, by using a monolithic source with high pulse-to-pulse stability that allows for long integration times; efficiency, by using pulsed laser sources that typically have higher wall-plug efficiency than continuous wave lasers; self-referencing, since the chirp rate is fixed by physical properties of the system, the coherent detection scheme does not depend on synchronization to an external component, and is robust against system drift; and time gating, which leads to higher signal to noise ratio for the same average power.

The technique is also compatible with broadband sources, such as quantum cascade laser (QCL) arrays. In such system, an array of distributed feedback (DFB) lasers is defined on a semiconductor chip, with each DFB laser addressable individually. The emission wavelength of each laser in the array can be selected arbitrarily at the time of fabrication, provided the emission wavelength is within the gain bandwidth of the laser material. Beam combining of the different lasers into a single beam can be achieved with techniques such as spectral beam combining.

The techniques presented here enable coherent gain with laser arrays and other broadband sources. For instance, CDHS is compatible with pulsing the lasers in a laser array in a repeated sequence such that each laser in the array is pulsed a single time before completing the sequence and repeating. This is possible because the information carried by the heterodyne modulation can be extracted on a pulse to pulse basis and does not require coherence of the heterodyne modulation across several averaged pulses. Time multiplexing allows fast frequency scans through the different lasers in arbitrary sequences.

CDHS is time gated and the heterodyne information is carried by each pulse. For example, a single 300 ns long pulse may carry a coherently amplified signal. The instantaneous amplitude and/or instantaneous phase can be retrieved from each pulse. And these quantities can be averaged over several pulses to increase the signal to noise ratio. In other words, we do not require coherence of the heterodyne beat across several pulses. Pulse-to-pulse phase jitter and speckle amplitude fluctuations are thus not concerns.

Accordingly, embodiments of the present technology include methods and systems for making a spectroscopic measurement of a sample. An example system includes a single-mode laser and a photodetector. In operation, the single-mode laser generates a chirped signal pulse with in response to an electrical pulse. The chirped signal pulse may be chirped due to at least one of heating of the single-mode laser by the electrical pulse or a carrier density change of the single-mode laser by the electrical pulse. The chirped signal pulse illuminates the sample, interacting with the sample to produce scattered, reflected, and/or transmitted light. The photodetector detects a heterodyne modulation caused by interference of the chirped signal pulse (scattered, reflected, and/or transmitted by the sample) and a chirped reference pulse generated with the single-mode laser. This heterodyne modulation depending on a dispersion and/or an absorption of the sample.

In some cases, the single-mode laser is a distributed feedback (DFB) laser (e.g., a DFB quantum cascade laser) that emits a chirped optical pulse having a pulse duration of about 10 nanoseconds to about 10 microseconds and a chirp rate ranging from about 0.2 wavenumbers per hundred nanoseconds to about 4 wavenumbers per hundred nanoseconds. In some cases, a beam splitter or other suitable device may split the chirped optical pulse into the chirped signal pulse and the chirped reference pulse. In other cases, the single-mode laser emits the chirped signal pulse at a first time and the chirped reference pulse at a second time different than the first time.

The system may include circuitry, such as a processor, that determines the dispersion and/or the absorption of the sample from the detected heterodyne modulation. For instance, this circuitry may estimate the dispersion of the sample based on the instantaneous phase. The circuitry may also estimate the absorption of the sample based on the instantaneous amplitude.

In some example, the single-mode laser (or possibly an array of single-mode lasers) emits multiple chirped signal and reference pulses. For instance, the chirped signal pulse may be a first chirped signal pulse, the electrical pulse may be a first electrical pulse, the chirped reference pulse may be a first chirped reference pulse, and the heterodyne modulation may be a first heterodyne modulation. In these example, the single-mode laser (or another single-mode laser) may generate a second chirped signal pulse with the single-mode laser in response to the second electrical pulse. This second chirped signal pulse interacts with the sample, then interferes with a second chirped reference pulse generated by the single-mode laser (or the other single-mode laser). (Optionally, a piezo-electric mounted mirror may dither a phase of the second chirped reference pulse with respect to a phase of the first chirped reference pulse.) The photodetector detects a second heterodyne modulation caused by the interference of the second chirped signal pulse and the second chirped reference pulse. This second heterodyne modulation depends on the dispersion and/or the absorption of the sample.

If desired, the circuitry may average the first heterodyne modulation and the second heterodyne modulation. In addition or instead, the circuitry may determine a second instantaneous phase of the second heterodyne modulation and average the second instantaneous phase with the instantaneous phase of the first heterodyne modulation. Similarly, the circuitry may determine a second instantaneous amplitude of the second heterodyne modulation and average the second instantaneous amplitude with the instantaneous amplitude of the first heterodyne modulation.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1 is a plot of an interference pattern generated using a chirp delay heterodyne measurement (upper trace). The modulation waveform is clearly measurable. The pulse width is about 300 ns. The detector is a MCT long wave (up to 11 μm) with D* of $6 \times 10^7$ cm·$\sqrt{Hz}$/W. For comparison the red trace shows the same measurement when the reference arm optics was blocked.

FIG. 2 is a schematic of a chirp delay heterodyne system. The equations represent the different terms constituting the heterodyne signal. The circuitry used to handle the detector signal may include amplifiers, filters, analog-to-digital converters (ADC), processors with corresponding memory, displays and means of interacting digitally with other equipment to report data, receive commands or firmware upgrades, etc.

FIG. 3A shows chirp delay heterodyne signal (solid line) with the reference arm alone (sample arm blocked) shown in dashed line.

FIG. 3B is a plot showing only the cosine modulated portion of the signal (per expression included). Perfect heterodyning should lead to an amplitude of 1. The actual amplitude observed is closer to 0.6, indicating imperfect mixing (interference) of the two waves (signal and reference) on the detector. Wave front aberration can cause such problems.

Figure 6:
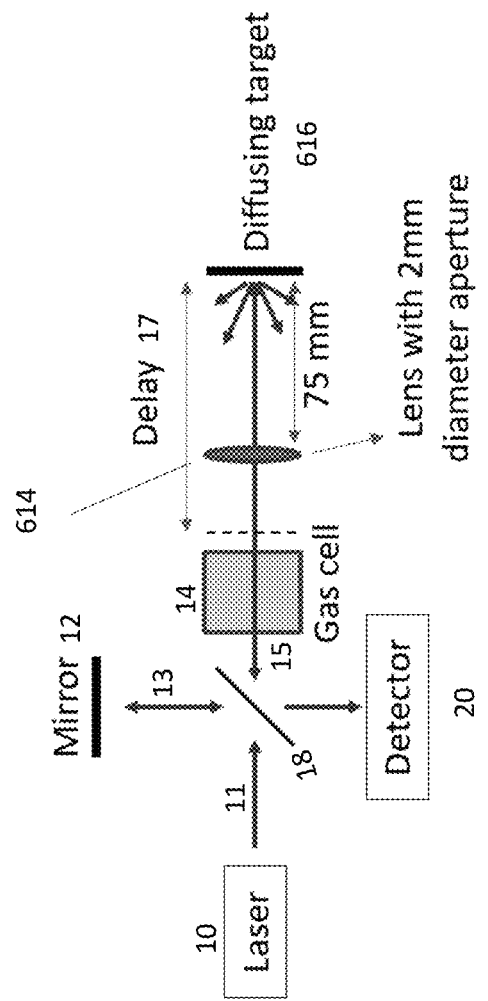

FIG. 6 is a schematic of a chirp delay heterodyne system that operates in the presence of speckle, depolarization, and pulse-to-pulse jitter effects. A return signal on the sample arm is generated by diffuse back-reflection off a rough target, such as sandblasted aluminum, plywood, or cardboard. The sample arm beam is focused onto the target using a lens, and a portion of the reflected signal is collected by the same lens.

Figure 7:
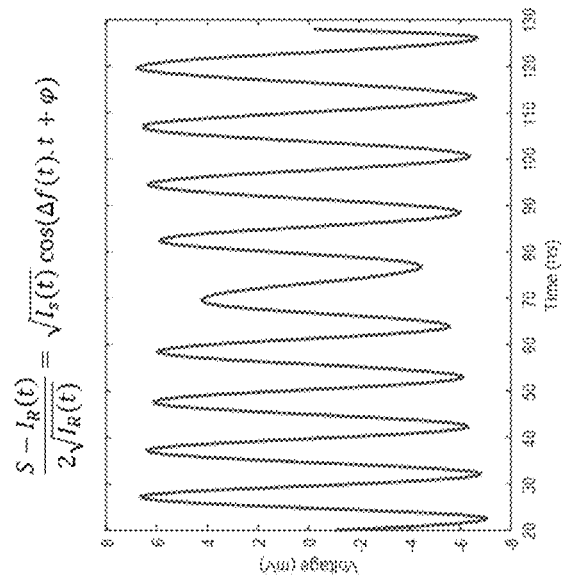

FIG. 7 is plot showing heterodyne modulation (as defined in the expression in inset) obtained after reflection off sandblasted aluminum using the system of FIG. 6. The trace is the average of 2000 pulses. The expected transmission through the sample arm, including finite collection efficiency of the diffusely scattered light, is $1.8 \times 10^{-4}$. This corresponds to an expected modulation amplitude of $\sqrt{T_S}$=13 mV. Experimentally, we observe a modulation depth of about 6 mV. This is to be compared with an expected signal of about 145 μV in the absence of heterodyne gain, and a detector rms noise of 1.1 mV at the detection bandwidth used (200 MHz).

Figure 8:
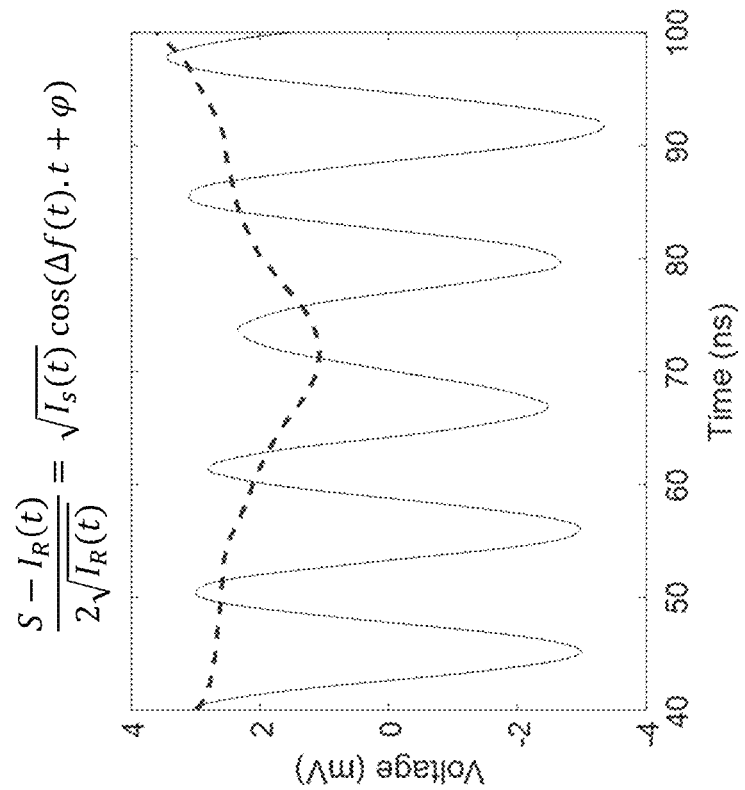

FIG. 8 is a plot showing heterodyne modulation (solid line; as defined in the expression in inset) obtained for a static rough reflector (zoom-in of the curve shown in FIG. 7). The dashed line represent the averaged instantaneous amplitude extracted from the analytic representation of the heterodyne signal obtained for each pulse. This data is obtained using a rough target, which introduces speckle. Furthermore, the rough target is moved during acquisition, such that this data set corresponds to a situation with time-varying speckle and phase jitter.

FIG. 9A is a plot of the heterodyne modulation obtained for a reflector in the sample arm that is fixed.

FIG. 9B is a plot of the heterodyne modulation obtained for a reflector that is vibrated along the optical axis to introduce phase jitter into the heterodyne modulation. By superposing the data from each pulse of a series of 2000 pulses, the underlying heterodyne modulation is blurred out, but the envelope is traced out.

Figure 9C:
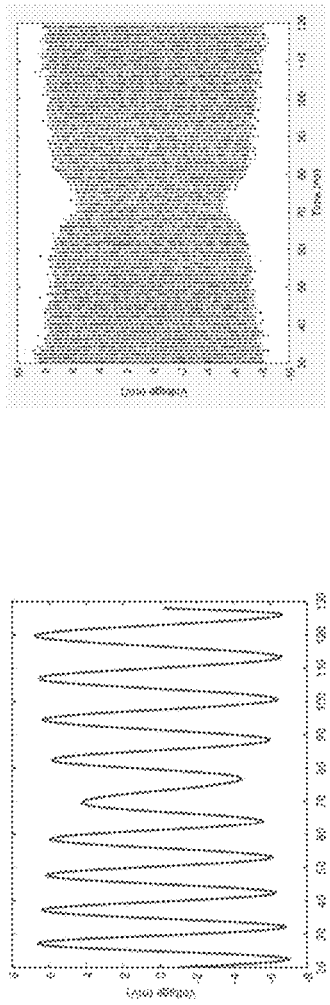
Figure 9C:
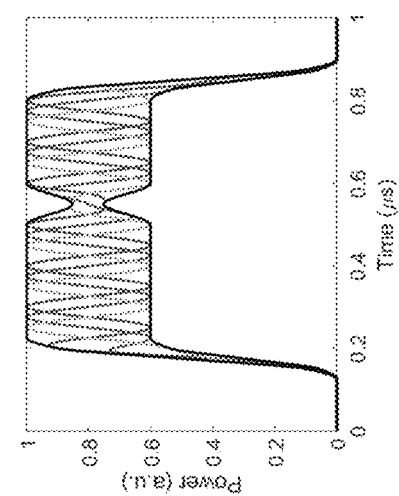

FIG. 9C is a schematic showing three heterodyne beats with three different phases contained within the same envelope. The vibration affects the phase of the heterodyne modulation for each pulse but the envelope is preserved, indicating that the heterodyne gain is preserved.

Figure 10:
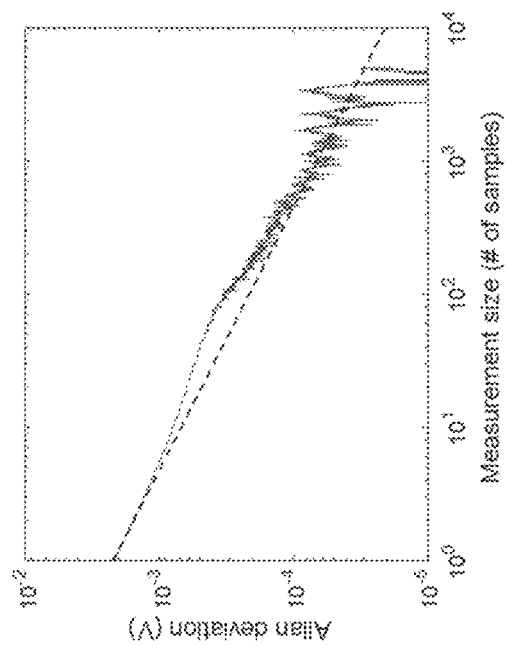

FIG. 10 is a plot of the Allan deviation (solid line) of the gas absorption dip depth retrieved by averaging instantaneous intensity data (dashed curve in FIG. 8). The dashed line shows expected trend (reduction of standard deviation as the square root of the number of samples).

Figure 11:
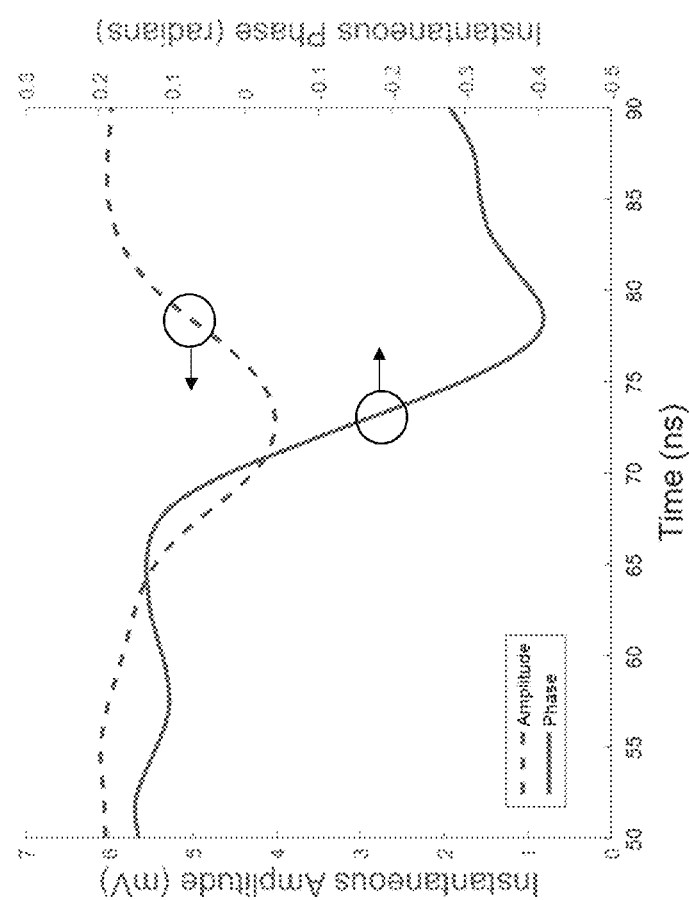

FIG. 11 is a plot of the instantaneous amplitude (dash) and the instantaneous phase (solid) of the heterodyne signal in solid line in FIG. 8. In this case, the amplitude and phase were extracted using the Hilbert Transform technique, although other retrieval methods can be used. The absorption and dispersion of the $CH_3D$ line are clearly visible in the vicinity of 70 ns.

Figure 2:
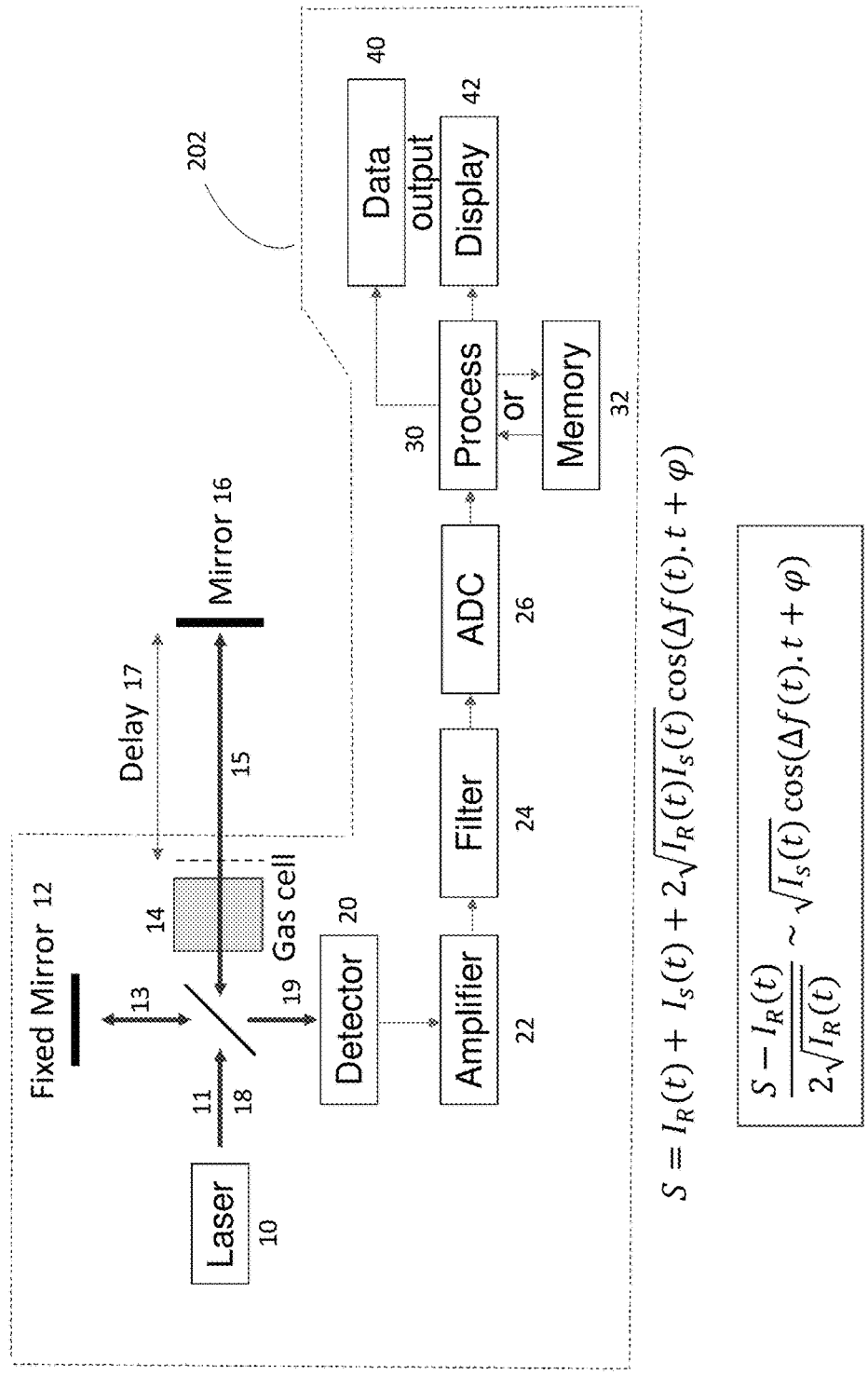
Figure 12C:
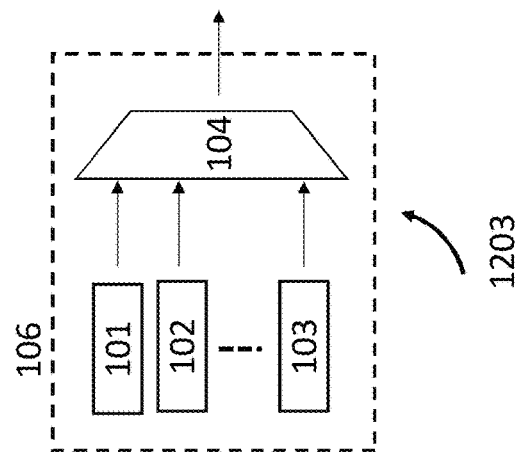
Figure 12B:
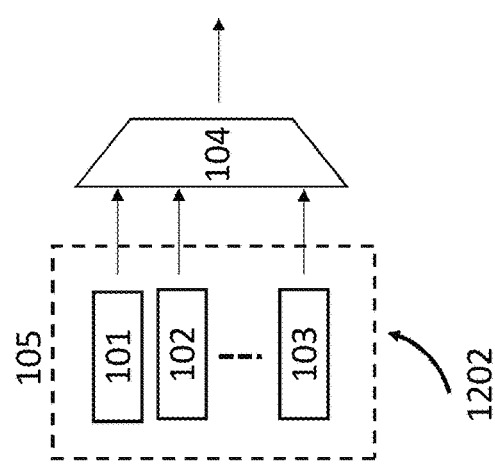
Figure 12A:
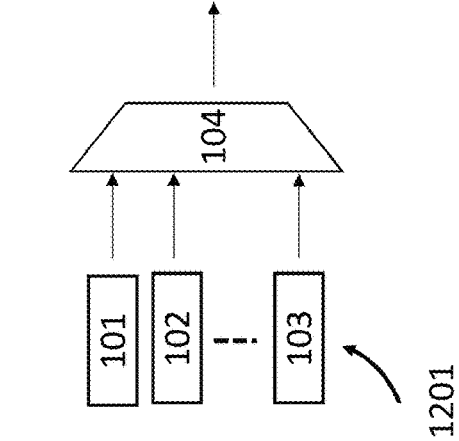

FIGS. 12A-12C show arrays of independent laser sources suitable for chirp delay heterodyne spectroscopy, e.g., in place of the laser sources shown in FIGS. 2 and 6.

Figure 13A:
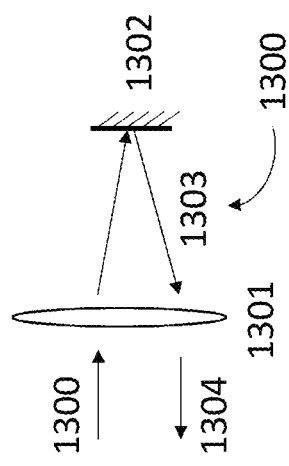
Figure 13B:
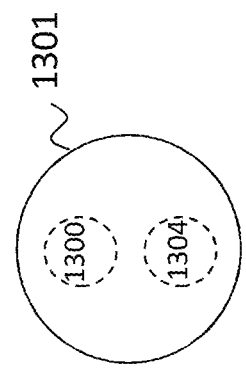

FIGS. 13A and 13B show side and on-axis views of a lens and reflector assembly that can be used to terminate the sample or reference arm.

Figure 14:
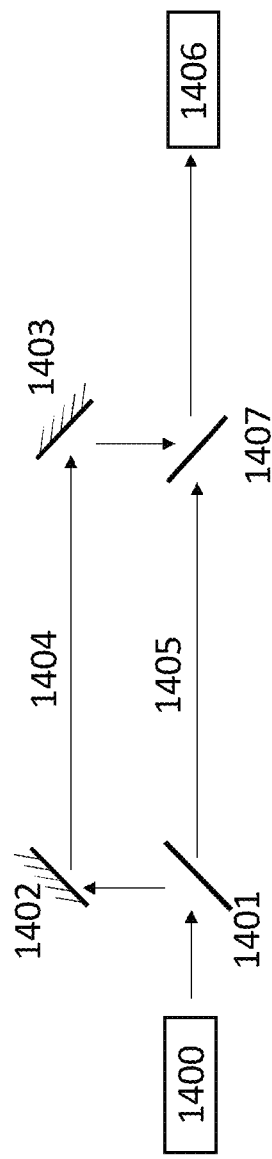

FIG. 14 shows an alternative optical architecture for chirp delay heterodyne measurements.

Figure 15A:
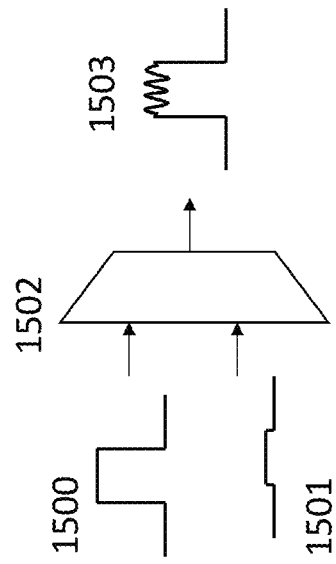
Figure 15B:
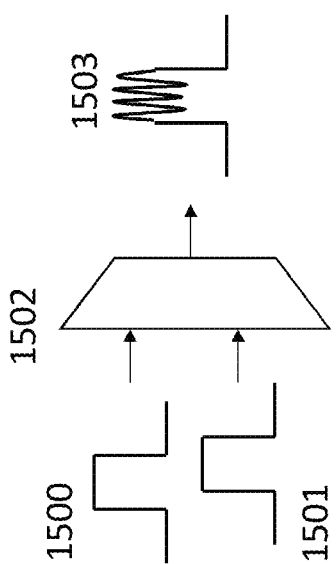

FIGS. 15A and 15B illustrate how the relative signal amplitude affects the heterodyne modulation amplitude.

Figure 16:
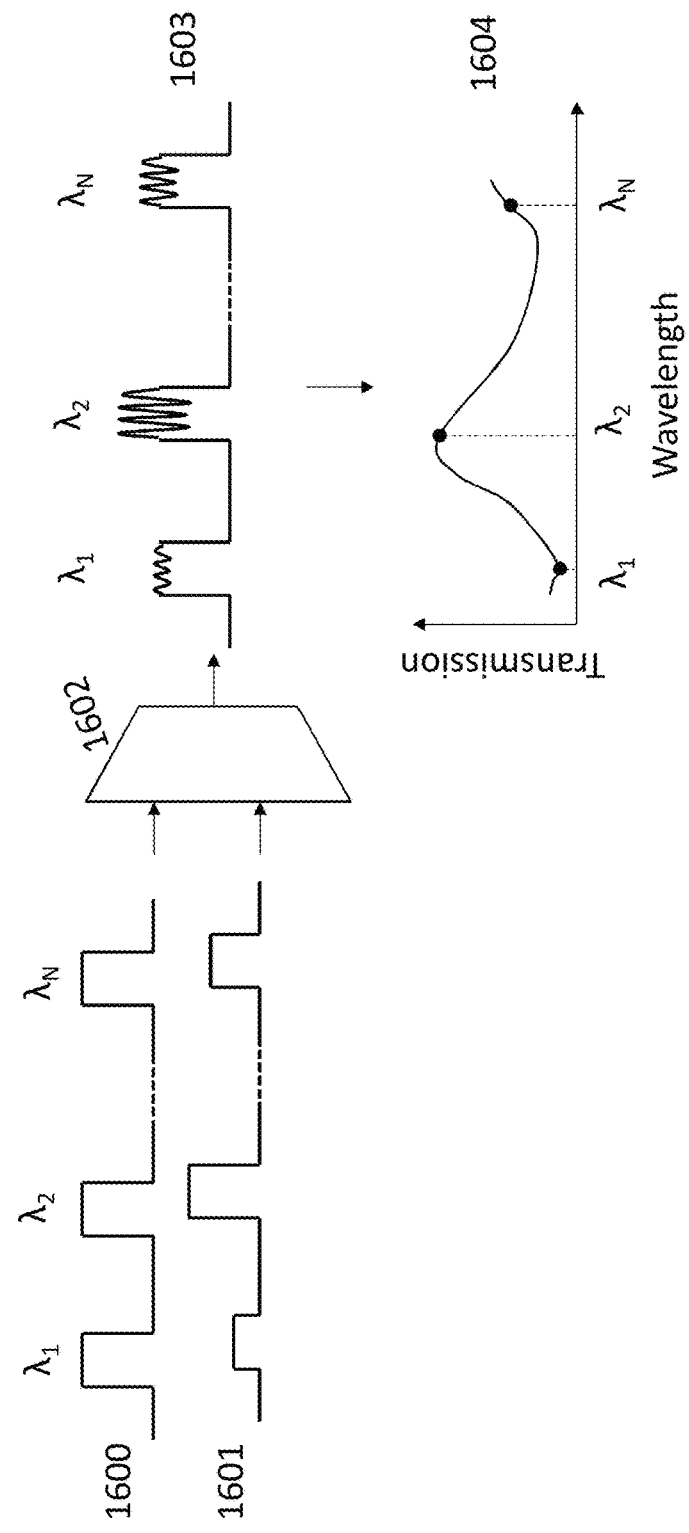

FIG. 16 illustrates a chirp delay heterodyne measurement made using a train of N consecutive pulses from N lasers, each of which emits at a different wavelength.

Figure 17:
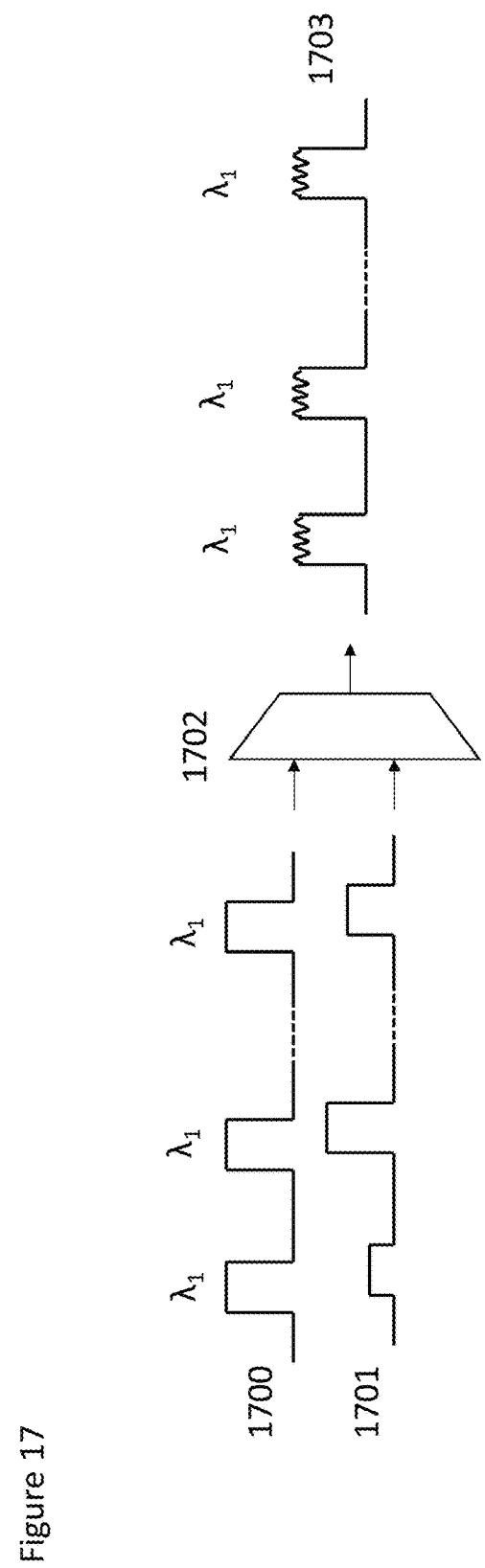

FIG. 17 illustrates a chirp delay heterodyne measurement made using a train of N consecutive pulses at the same wavelength.

Figure 18:
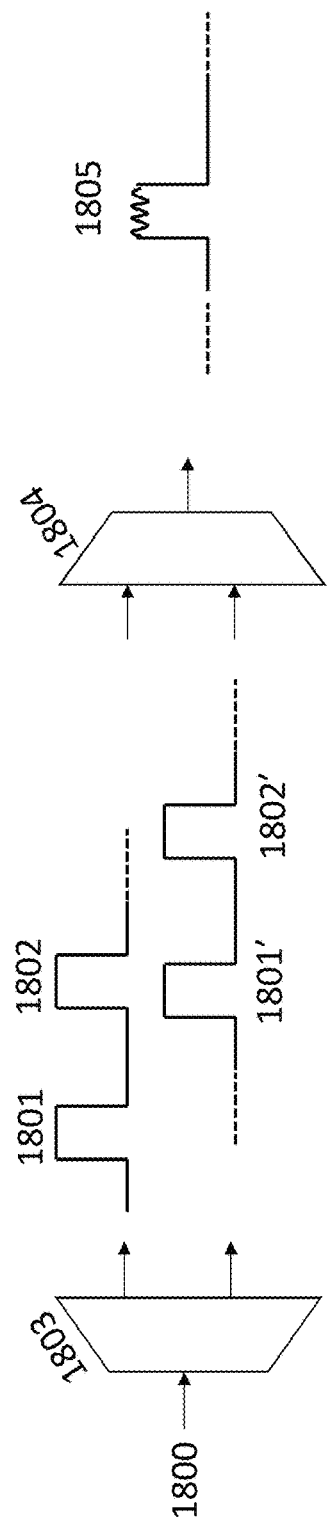

FIG. 18 illustrates a chirp delay heterodyne measurement made by interfering signal pulses with reference pulses emitted after the signal pulses are emitted.

Figure 19A:
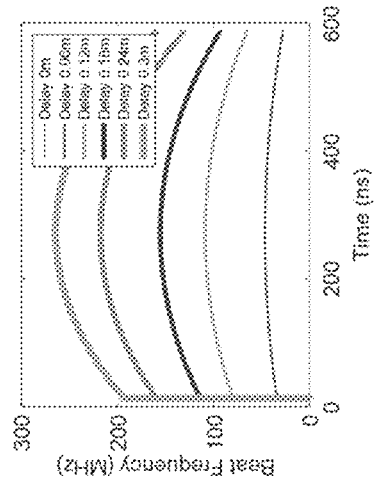

FIG. 19A is a plot of measured laser emission wavenumber vs time for a pulsed distributed feedback quantum cascade laser.

Figure 19B:
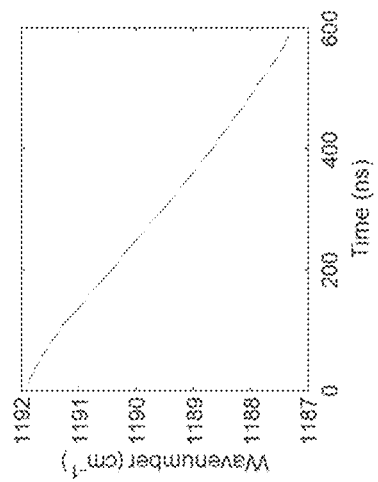

FIG. 19B is a plot of the beat frequency of the heterodyne modulation produced when two copies of the pulses from FIG. 19A interfere on a detector, with various optical path difference between the two copies as indicated in the legend.

DETAILED DESCRIPTION

We use the natural chirp of one or more pulsed single mode lasers (e.g., distributed feedback semiconductor laser, quantum cascade lasers, external cavity lasers using a diffraction grating or other frequency selective element, or other single-mode lasers) to produce a difference frequency between time-delayed reference and signal channels. Such chirp can occur as a response to an electrical drive pulse via different mechanisms including heating of the laser active region or change in carrier density in the laser material. An arbitrary waveform generator can be used to create the electrical pulse driving the laser, in order to control the shape of the time variation of the instantaneous laser frequency. Additionally, an integrated amplitude or phase modulator can be fabricated on the same chip as the semiconductor laser and used to create a chirp during the duration of the electrical pulse driving the laser. Such modulator could be controlled independently from the laser drive, and control the shape of the time variation of the instantaneous laser frequency.

Figure 1:
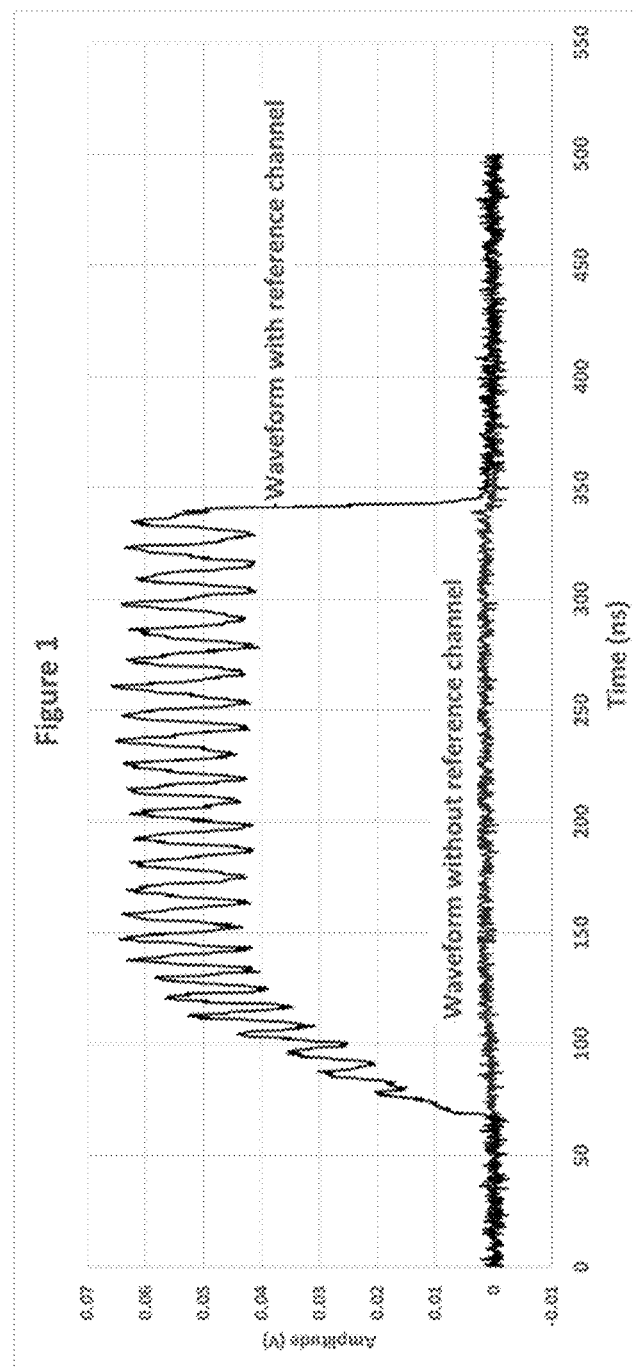

For a system or array with many lasers, each operating at a different wavelength, the chip-delay instantaneous intensity detected for the $i^{th}$ laser in the system can be expressed as:

$$P(t)_{CD,i} = P(t)_{ref,i} + P(t)_{s,i} + 2\sqrt{P(t)_{ref,i} \cdot P(t)_{s,i}} \cdot \cos\left[(\omega_{ref,i}(t) - \omega_{s,i}(t))t + (\varphi_{ref,i} - \varphi_{s,i})\right]$$

where $P(t)_{ref,i}$ is the instantaneous reference pulse intensity, $P(t)_{s,i}$ is the instantaneous signal pulse intensity, $\omega_{ref,i}(t)$ and $\omega_{s,i}(t)$ are the instantaneous frequencies of respectively the reference and the signal, with their time variation accounting for the chirp of the laser, and $\varphi_{ref,i}$ and $\varphi_{s,i}$ are the corresponding phases. The reference signal can be tapped off by an optical beam splitter from the laser source. The rest of the laser light forms the signal and interacts with a substance that scatters, reflects, and/or transmits the incident light. The scattered, reflected, and/or transmitted light is collected and interfered with the reference and is represented here as $P(t)_{s,i}$. The frequency shift between reference and signal resulting from different optical lengths in the two channels is $\Delta\omega_i(t) = [\omega_{ref,i}(t) - \omega_{s,i}(t)]$. This frequency difference is itself generally time dependent unless the chirp of the laser is linear (FIG. 1). The chirp of the laser, accounted for by the time variation of the instantaneous laser frequency $\omega_{ref,i}(t)$, can be characterized a priori and can be assumed to be a known function for lasers such as semiconductor distributed feedback lasers, repeatable from pulse to pulse and over time. The phase term $\Delta\varphi = (\varphi_{ref,i} - \varphi_{s,i})$ is dependent on the delay between arms. When the signal arm is tapped off the reference this term is zeroed out.

The time variation of the instantaneous laser frequency $\omega_{ref,i}(t)$ can be designed to some extent. For example, varying the doping concentration in the laser material can affect how much heat is dissipated in the active region in response to a given electrical pulse, and therefore can affect the tuning rate. Alternatively, the shape of the electrical pulse can be modified to shape $\omega_{ref,i}(t)$. A synthesized electrical pulse generated by an arbitrary waveform generator or other circuitry can be used to that effect.

For a case in which the signal reproduces the pulse but with only an amplitude change (i.e., the object does not introduce additional frequency or phase shift on the signal laser beam), the difference frequency is due to a time delay $$\tau = \frac{\Delta L}{c} \cdot n$$

n between signal and reference, where $\Delta L$ is the geometric length difference between the reference and signal paths, and c is the speed of light, and n is the effective refractive index of the propagation medium (n=1 for air):

$$\Delta\omega(t)_i = [\omega_{ref}(t) - \omega_s(t)] = [\omega_{ref}(t) - \omega_{ref}(t+\tau)]$$

The effective path length difference between the two channels can also contain contributions from dispersive effects (variation of refractive index with frequency of laser, phase shifts at interfaces, etc.).

In the limit of a non-dispersive propagation or an absorption process that can be approximated by an amplitude change over the range of laser chirped frequency, $\Delta\omega(t)_i$ is a known function of a single scalar parameter $\tau$, the time delay between signal and reference arm, independent of laser frequency. Fitting $\tau$ results in a measure of delay (e.g., thickness of the object). In a general dispersive case, $\tau$ is a function of laser frequency. Knowledge of the laser chirp can be assumed for lasers for which it is a repeatable function (from pulse to pulse, over time) that can be characterized a priori. Such knowledge can be leveraged to retrieve the function $\tau(\lambda)$ in the dispersive case.

The absorption of the signal is of interest can be retrieved from the normalized signal $$S_i = \frac{P(t)_{s,i}}{P(t)_{ref,i}}.$$

In the limit case of homodyne detection (equal path lengths between reference and signal, $\Delta\omega_i(t)=0$ and $\Delta\varphi=0$), $S_i$ can be calculated by:

$$S_i = \frac{P(t)_{s,i}}{P(t)_{ref,i}} = \frac{1}{4}\left[\frac{P(t)_{CD,i}}{P(t)_{ref,i}} - 1\right]^2$$

where it is assumed $P(t)_{s,i} \ll P(t)_{ref,i}$. Note that the measurement is not sensitive to laser power fluctuations since both $P(t)_{s,i}$ and $P(t)_{ref,i}$ are proportional to the source laser power. The signal $S_i$ is related to the absorption A of an analyte present in the path of the signal: $S_i = M \cdot A$, where M is the instrument transfer function.

In the general case of non-zero delay, different measurement modalities are possible to extract $S_i$, depending on whether the beat frequency $\Delta\omega(t)_i$ is time varying or constant in time. For simplicity, we neglect the term $\varphi_{ref,i} - \varphi_{s,i}$ in the following discussion. This term can be expressed as a function of $\tau(\lambda)$, and its exclusion does not change the discussion qualitatively since the remaining term in the cosine ($\Delta\omega(t)_i t$) is also a function of $\omega_{ref,i}(t)$ and $\tau(\lambda)$. If the beat frequency is constant (as is usually the case in heterodyne detection methods), then signal extraction methods such as band-pass filters or lock-in amplifiers can be used to filter the signal. If the beat frequency is time varying, but a known function $\Delta\omega(t)_i$, $S_i$ can be extracted from a measurement of $P(t)_{CD,i}$ and $P(t)_{ref,i}$:

$$S_i = \frac{P(t)_{s,i}}{P(t)_{ref,i}} = \frac{1}{4}\left[\frac{P(t)_{CD,i}}{P(t)_{ref,i}} - 1\right]^2 \bigg/ \cos^2(\Delta\omega(t)_i t)$$

It can be advantageous to measure $$\frac{P(t)_{CD,i}}{P(t)_{ref,i}}$$

in the analog domain (before digitization) to minimize errors due to digitization. If two detectors are used to measure $P(t)_{CD,i}$ and $P(t)_{ref,i}$, their respective outputs can be sent into a logarithmic amplifier to calculate $$\log(P(t)_{CD,i}) - \log(P(t)_{ref,i}) = \log\left(\frac{P(t)_{CD,i}}{P(t)_{ref,i}}\right)$$

in the analog domain.

The time varying beat frequency can be determined by a fit of $$\left[\frac{P(t)_{CD,i}}{P(t)_{ref,i}} - 1\right] = 2\sqrt{\frac{P(t)_{s,i}}{P(t)_{ref,i}}} \cos(\Delta\omega(t)_i t)$$

to find the parameter $\tau(\lambda)$ such that:

$$\Delta\omega(t)_i = [\omega_{ref}(t) - \omega_s(t)] = [\omega_{ref}(t) - \omega_{ref}(t+\tau(\Delta))]$$

assuming knowledge of the laser chirp function $\omega_{ref}(t)$.

If the chirp is not well characterized and the time delay is unknown (both $\omega_{ref}(t)$ and $\Delta\omega(t)_i$ are unknown), it may still be possible to extract $$\frac{P(t)_{s,i}}{P(t)_{ref,i}}$$

by analyzing the envelope of $$\frac{1}{2}\left[\frac{P(t)_{CD,i}}{P(t)_{ref,i}} - 1\right] = \sqrt{\frac{P(t)_{s,i}}{P(t)_{ref,i}}} \cos(\Delta\omega(t)_i t),$$

assuming in particular that $P(t)_{ref,i}$ and $P(t)_{s,i}$ vary slowly compared to the modulation frequency the heterodyne signal $\Delta\omega(t)_i$.

Another analog electronic operation that can be useful to perform on $P(t)_{CD,i}$ before digitizing the signal is to use a high-pass filter to remove the low frequency content of the underlying optical pulse $P(t)_{ref,i}$ and pass through the higher frequency modulation of $$\sqrt{\frac{P(t)_{s,i}}{P(t)_{ref,i}}} \cos(\Delta\omega(t)_i t)$$

relevant term. For example, if the pulse $P(t)_{ref,i}$ is shaped (e.g., using synthesized electronic laser pulse driver) to have a bounded electrical spectrum with limited high frequency tails (e.g., smooth rising and falling edges) a low pass cut-off filter can block the low electrical frequency part of the pulse and pass through the modulation at higher frequency defined by chirp delay frequency content $\Delta\omega(t)_i$. It might then be advantageous to make $\Delta\omega(t)_i$ at higher frequency to facilitate such electrical frequency filtration. Once the bulk of amplitude under the modulation (i.e., the slow varying $P(t)_{ref,i}$ term) is removed from $P(t)_{CD,i}$ the relevant signal term $$2\sqrt{\frac{P(t)_{s,i}}{P(t)_{ref,i}}} \cos(\Delta\omega(t)_i t)$$

would have an average of zero and can effectively be amplified by an adjustable-gain RF analog amplifier before analog-to-digital conversion.

We have implicitly assumed so far that $P(t)_{s,i}$ is proportional to $P(t)_{ref,i}$, implying constant transmission of the signal over the frequency range of the chirp. This is a good approximation if materials with broad absorption features are in the signal path. However, the notations used are more general. If an object or substance in the signal path has non-constant transmission through the spectral range of the chirp (e.g., narrow gas absorption line with FWHM comparable or smaller than laser frequency chirp) then the absorption line multiplies the amplitude of the heterodyne modulation term. In other words:

$$P(t)_{s,i} \rightarrow P(\omega(t))_{s,i}$$

and simple decoupling of the modulation into amplitude and cosine function may not hold. However as long as the frequency dependence of amplitude $P(\omega(t))_{s,i}$ is slow compared to the frequency dependence of the cosine term in $\Delta\omega(t)_i t$, the amplitude of the modulation can be measured by fitting and the shape and intensity of absorption line can be obtained. If narrow absorption features are expected, it may thus be desirable to choose a large heterodyne beat frequency by introducing a large optical path length difference between the signal and reference arms and using a detector with a large bandwidth to detect this high speed modulation.

Similar to other coherent measurements, the ultimate signal-to-noise of $S_i$ may be limited by shot noise of the signal $P(t)_{s,i}$.

Similar to other coherent measurements, the coherent gain is:

$$G_i = \frac{2\sqrt{P_{ref,i} \cdot P_{s,i}}}{P_{s,i}} = 2\sqrt{\frac{P(t)_{ref,i}}{P(t)_{s,i}}}$$

If N lasers, referred here by index $i=0, \ldots, N$, are used to interrogate optical, chemical, and other properties of substances or objects, then we have realized a chirp-delay heterodyne measurement or spectroscopy.

Variations on Chirp Delay Heterodyne Measurements and Chirp Delay Spectroscopy

To keep $\Delta\omega(t)_i$ below the cutoff frequency of the detector, one can use a delay line for the reference optical arm to reduce the optical path length difference between reference and signal arm.

It can be desirable to dither the phase of one beam (e.g., the reference beam) with respect to the phase of the other beam (e.g., the signal beam), for example, by vibrating a folding return mirror on the reference path using a piezo-electric actuator. In the limit of small vibration amplitude, the dither appears as a time shift (phase shift) of the heterodyne modulation. The magnitude of this shift is larger when the pulse chirp rate $$\left(\frac{d\omega_{ref}}{dt}\right)$$

is larger. Each pulse has a set of amplitudes and relative times (from start of the pulse) for the peaks and valleys defining the modulation. Different pulses have different time (phase) shifts, hence the positions of the peaks and valleys is different. A scatter plot of peaks and valleys against relative time indicates the envelope of the underlying modulation. For an unknown chirp or time delay, and in the case of narrow absorption lines, the amplitude of modulation can thus be obtained.

For distances where the delay of signal pulse becomes comparable to pulse width, it is possible or even desirable to use a second pulse generated by the same or a similar single mode laser as a reference beam to adjust the signal to reference arm delay arbitrarily using two electronic pulses with controlled and adjustable delay. For example, if the delay is 1 µs and the pulse width is 300 ns, one can use a second pulse, for example, from the same laser source, to generate a reference pulse delayed by about 1 µs from the signal pulse to ensure overlap in time of the signal pulse and the reference pulse on the detector. The chirp and pulse shape of typical DFB lasers is very reproducible so the beat modulation detected may have high signal integrity using two sequential pulses. We call this modification of chirp-delay measurement a double-pulse chirp-delay measurement or spectroscopy.

In this case, the signal and reference pulses are generated from different laser pulses, whereas in other cases, both pulses are generated from a single laser pulse, using, for example, a beam splitter. In the case of reference and signal pulses generated from different laser pulses, an unknown phase y is added to the heterodyne signal:

$$P(t)_{CD,i} = P(t)_{ref,i} + P(t)_{s,i} + 2\sqrt{P(t)_{ref,i} \cdot P(t)_{s,i}} \cos[(\omega_{ref,i}(t) - \omega_{s,i}(t))t + \varphi_{s,i}]$$

For each pair of reference and signal pulses measured, this phase $\varphi_{s,i}$ might be different. Using same approach as indicated above the scatter plot of peak and valleys versus relative time can enable to trace out the envelope of the modulation in order to retrieve arbitrary signal or narrow absorption lines.

The pair of reference and signal pulses can also be generated from two separate lasers, assuming their difference frequency is relatively small (e.g., less than a few gigahertz), so that the heterodyne modulation frequency is within the detection bandwidth of the detector. Since the two lasers are not necessarily phased-locked to one another, both the phase $\varphi_{s,i}$ and the beat frequency $\omega_{ref,i}(t) - \omega_{s,i}(t)$ may vary from pair of pulses to pair of pulses, but as described here, our time-gated method is robust against phase jitter and variations of heterodyne beat frequency. This is in contrast to most existing heterodyne techniques, which typically require a stable, coherent heterodyne beat, with a detection system that typically attempts to measure the amplitude of that heterodyne beat.

If the delay between signal and reference pulse is chosen to be zero, then homodyne detection is achieved. This can be advantageous for use with slower detector with lower bandwidth.

Experimental Results

We demonstrated coherent gain using the system shown in FIG. 2. This system includes a laser source 10—here, a quantum cascade laser—that emits pulses 11 with a peak power of 80 mW and a center wavelength of 9.2 µm. The laser source 10 was pulsed at a 10 kHz repetition rate with electrical pulses having a 300 ns pulse duration. Each electrical pulse is a square wave and heated the laser cavity, causing a red shift in the output wavelength of the laser source 10—in other words, heating by the constant-amplitude electrical pulse chirps the pulse emitted by the laser source 10. The chirp was not necessarily linear (i.e., the chirp rate changed as a function of time), but was repeatable from pulse to pulse, possibly because the laser cavity cooled between pulses.

A beam splitter 18 in optical communication with the laser source 10 split each pulse 11 into a reference pulse 13 and a signal pulse 15. The reference pulses 13 propagated along a reference arm to a fixed mirror 12, which reflected them back to the beam splitter 18. The signal pulses 15 propagated along a signal arm with a sample—here, a gas in a gas cell 14—and a delay 17 to a mirror 16, which reflected them back through the gas cell 14 to the beam splitter 18. The mirror 16 could be fixed or could move along the optical axis of the signal arm to vary the delay 17.

The beam splitter 18 recombined each reference pulse 13 with a corresponding signal pulse 15 to form a recombined beam 17 that illuminated a detector 20. In this case, the detector 20 was a room temperature (uncooled) photovoltaic mercury-cadmium-telluride (MCT) detector with a 100 MHz 3 dB bandwidth and a detectivity of $2 \times 10^7$ cm.Hz$^{1/2}$/W. The detector 20 was coupled to an amplifier 22 that amplified the electrical signal emitted by the detector 20 in response to the interference of the recombined reference and signal pulses on the detector 20. A filter 24 filtered low-frequency noise and any DC bias to yield a heterodyne modulation signal. The filter 24 was coupled to an analog-to-digital converter (ADC) 26, which in this case was an off-the-shelf USB-scope with 12 bits of vertical resolution, a 200 MHz bandwidth, and a 500 MS/s sampling rate. The ADC 26 digitized the heterodyne modulation signal for processing (e.g., instantaneous amplitude/phase determination, averaging, etc.) by a processor 30. The processor 30 stored this information in a memory 32 and provided it, in raw and/or processed form, as a data output 40 suitable for rendering on a display 42.

Some or all of the optical and electronic components may be disposed within a protective housing 202 made of plastic, metal, or any other suitable material. If desired, the housing 202 can be mounted on a static mount or a moveable platform. In some cases, the optical and electronic components are small enough and light enough to fit within a handheld or man-portable package.

Figure 3B:
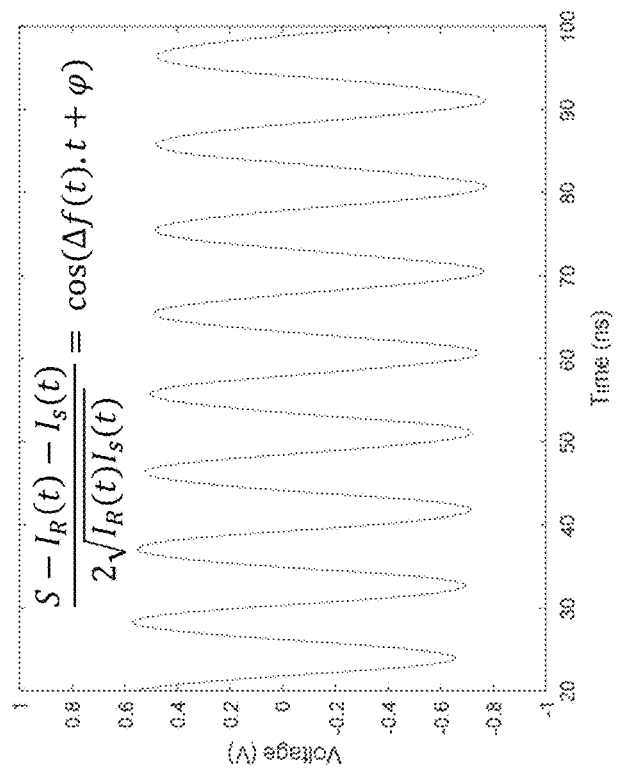
Figure 3A:
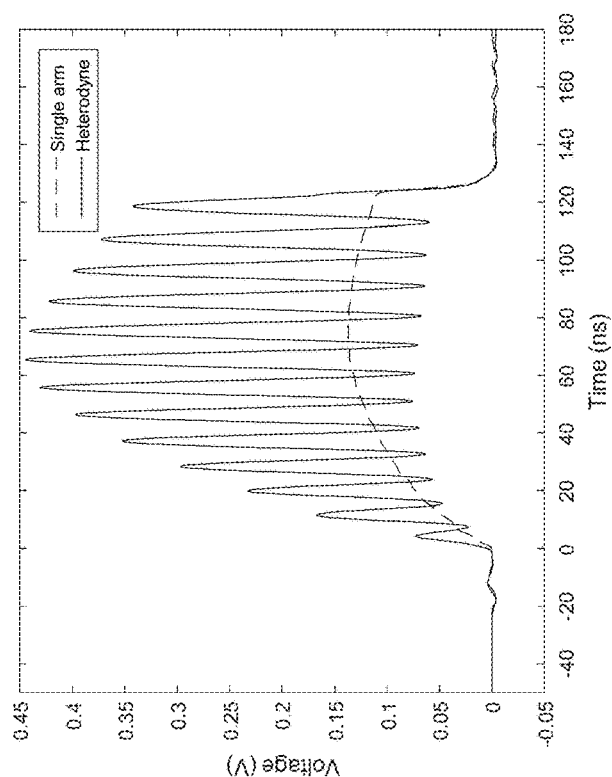

The heterodyne signal is illustrated in FIG. 3A, in a situation with low attenuation of the sample arm ($I_S \sim I_R$). Perfect heterodyning should lead to an amplitude of 1 for the modulation shown in FIG. 3B. The actual amplitude observed is closer to 0.6, indicating imperfect mixing (interference) of the two waves (signal and reference) on the detector. Wave front aberration can cause such problems. The maximum SNR that can be obtained is limited by the dynamic range p of the detector:

$$SNR = \frac{2\sqrt{I_R I_S}}{\sigma_N} = 2\rho\sqrt{T}$$

with $\rho = I_R / \sigma_N$ and $I_S = T \cdot I_R$

For example, if $\rho=1000$ and a minimum SNR of 2 is desired, the minimum transmission that can be detected (with SNR=2) is:

$$T_{min} = \left(\frac{SNR}{2\rho}\right)^2 = 1 \times 10^{-6}$$

Figure 4A:
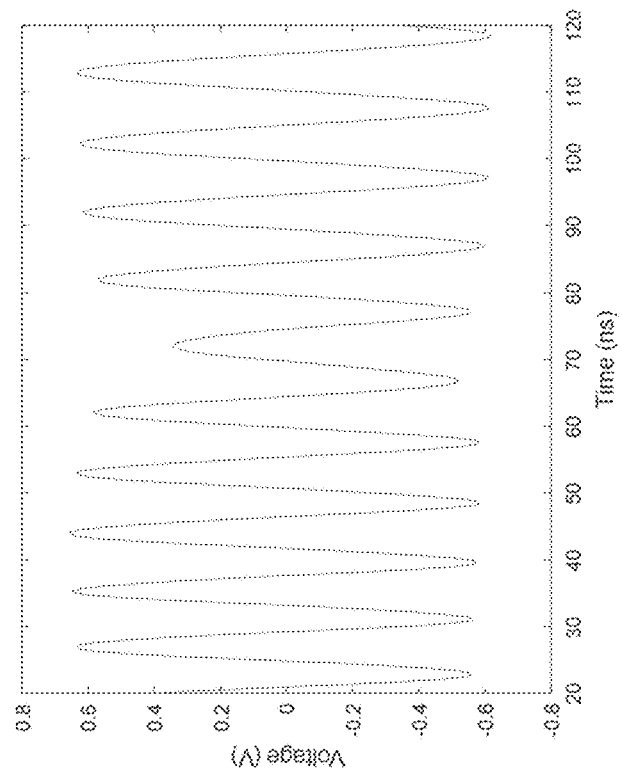
FIG. 4A is a plot of a signal with sample arm alone (reference arm blocked), with a gas cell inserted along path, shown in dashed line, heterodyne signal with both arms enabled in solid line.
Figure 4B:
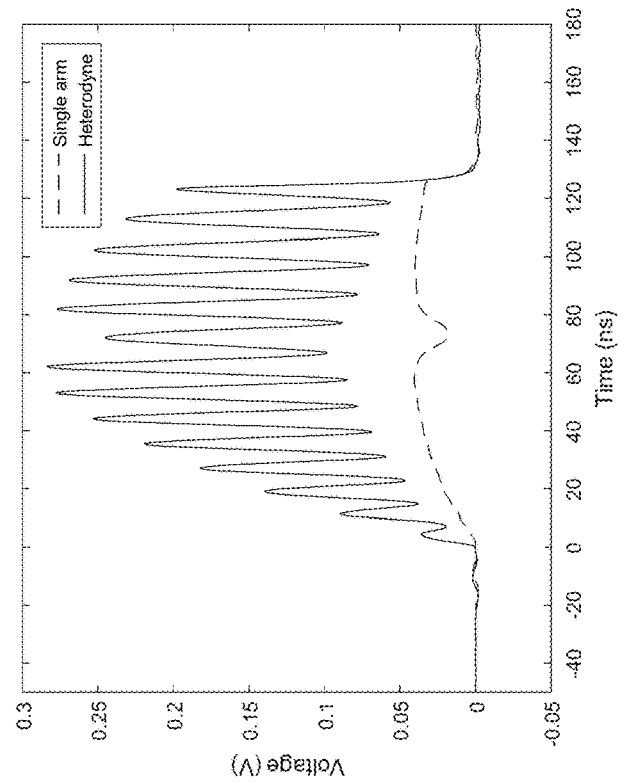
FIG. 4B is a plot showing only the cosine modulated portion of the signal.

In FIGS. 4A and 4B, we show the results of an experiment combining chirp delay heterodyne spectroscopy with intrapulse spectroscopy. In this case, a 5-cm-long gas cell containing methane ($CH_3D$) at 17 Torr, which is a gas that absorbs at the laser wavelength, was inserted in the sample arm.

Over the duration of the electrical pulse driving the laser (from a few nanoseconds to a few microseconds in duration, typically), the electrical energy dissipated in the laser active region leads to an increase in temperature, affecting in turn the effective refractive index $n_{eff}$ of the laser waveguide mode. For a distributed feedback laser, a grating is etched on top of the active region with a period $\Lambda_g$. The grating provides feedback such that the laser is more likely to operate on a single mode with wavelength $\lambda=2\, n_{eff} \Lambda_g$ (for a first order grating). When the laser active region heats up as a result of Joule heating, $n_{eff}$ increases and the laser emission wavelength red-shifts (i.e., the wavelength increases).

Therefore, over the duration of the electrical drive pulse, the wavelength of the laser is red-shifting and the can thus scan over the absorption line of a gas. In FIG. 4A, we can observe a dip in the transmission of the single arm experiment that corresponds to the wavelength of the laser scanning through a gas absorption line. In other word, the chirp of the laser enables mapping the wavelength-dependent transmission due to the presence of a narrow absorption line into a time dependent transmission, as shown in FIG. 4A.

This time dependent transmission is embedded in the heterodyne signal as a time-dependent envelope of the modulation. This is better illustrated in FIG. 4B which shows the modulated portion of the heterodyne signal (as in FIG. 3B). The dip in the envelope corresponding to the gas absorption can be seen.

Figure 5B:
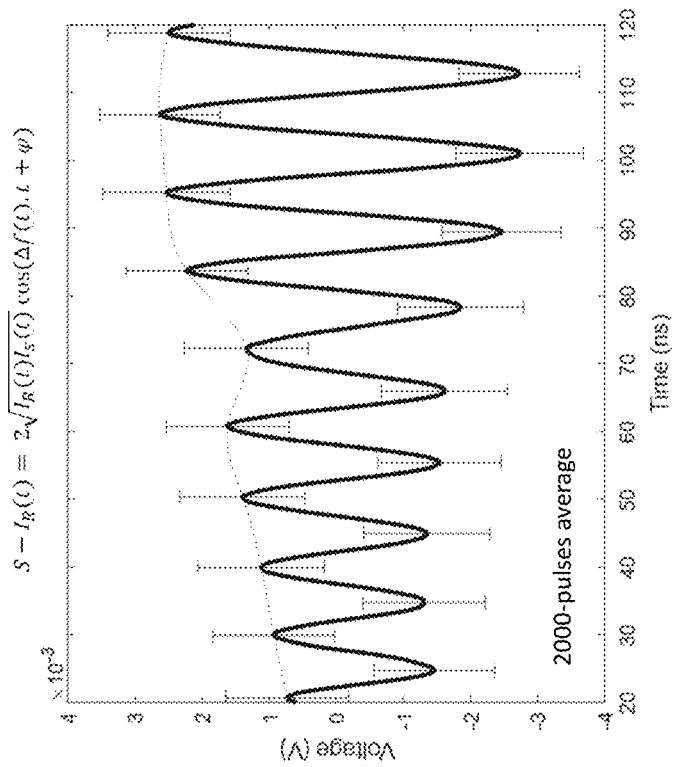
FIG. 5B is a plot showing only the modulated portion of the signal, as indicated by the inserted formula. The envelope is traced out to guide the eye, as well as error bars with a total length of two standard deviations of the signal, shown at the heterodyne signal peaks.
Figure 5A:
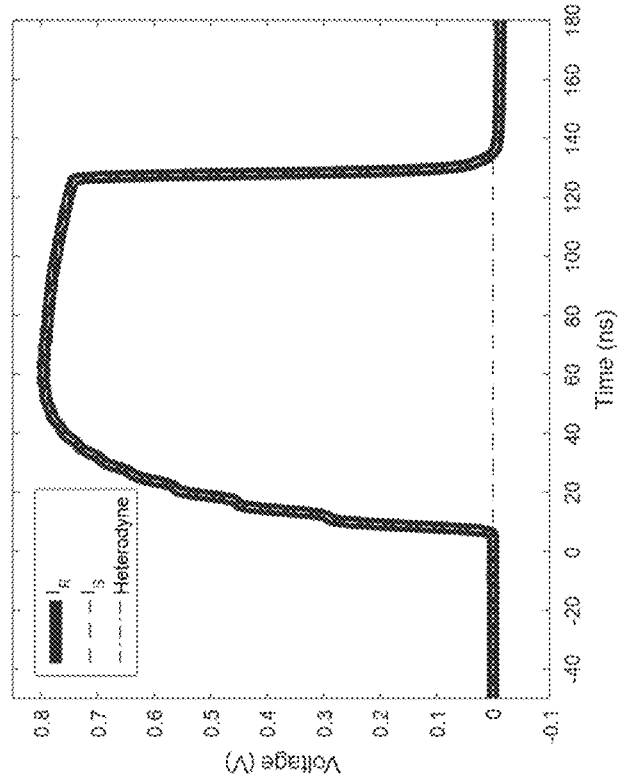
FIG. 5A is a plot of a signal with reference arm alone (sample arm blocked) shown in thick solid line, signal with signal arm alone (reference arm blocked) shown in dashed line, heterodyne signal with both arms enabled in white dash-dot line.

FIGS. 5A and 5B show results obtained with a setup similar to the one in FIG. 2, with a gas cell in the sample arm. In addition, we add a neutral density filter to attenuate the signal transmitted through the signal arm by a factor $10^4$, corresponding to two passes through a single neutral density filter with an attenuation of $10^2$. Transmission through the gas cell adds an extra attenuation factor of 3, such that the overall transmission of the signal through the sample arm is attenuated by a factor $3\times10^4$. Without this attenuation, the detector signals received for sample and reference arms were both $I_R=I_S=0.8$ V. Attenuation reduced the sample arm signal to $I_S=24$ µV. This is to be compared with a root-mean-square (rms) noise of 1.1 mV for the detector used, with no averaging and a 200 MHz bandwidth. As a consequence, extracting the sample arm signal would require extensive integration, eventually limited by system drift. When enabling both arms in order to obtain the heterodyne modulation, the amplitude of the expected modulation is $2\sqrt{I_R I_S}=8.8$ mV. Experimentally, we observe in FIG. 5B a modulation amplitude of about 2.5 mV. An etalon in the neutral density filter explains the slow envelope amplitude modulation. As a consequence, the heterodyne gain allows us to measure the sample arm transmission with significantly less averaging. The experimental gain obtained is about 100, corresponding to $10^4$ less averaging time required to obtain the same signal-to-noise ratio (assuming the noise observed is reduced as the square root of the integration time).

Robustness Against Speckle, Phase Jitter, and Depolarization

In the next few paragraphs, we discuss the robustness of the technique against speckle effects, depolarization effects, phase-jitter (modulation of the delay between the two arms). These effects can be introduced for example by using reflection off a rough target to generate a return signal on the sample arm (speckle and depolarization), or by having a time varying optical delay between the reference and sample arms (for example, by using a moving target with respect to the rest of the instrument to generate a return signal on the sample arm, or if atmospheric turbulences in a long open-path sample arm affect the transmission).

FIG. 6 shows a system like the one shown in FIG. 2 with a lens 614 and a diffusing target 616 in the sample arm. (The reference arm could have a lens and/or a diffusing target as well or instead.) The return signal 15 on the sample arm is now generated by diffuse back-reflection off the diffusing target 616, which may include sandblasted aluminum, plywood, or cardboard. The sample arm beam is focused onto the target 616 using the lens 614, and a portion of the reflected signal 15 is collected by the same lens 616. In our experimental setup, the lens 616 had a 2 mm diameter aperture and a 75 mm focal length. The lens's collection efficiency is thus equivalent to that of a 2-inch diameter lens with a 1.9-meter standoff distance from instrument to target. The rest of the setup is the same as described above with respect to FIG. 2.

We show in FIG. 7 the heterodyne modulation obtained after reflection off sandblasted aluminum. The trace is the average of 2000 averages. The expected transmission through the sample arm, including finite collection efficiency of the diffusely scattered light, is 1.8×10-4. This corresponds to an expected modulation amplitude of $\sqrt{I_S}=13$ mV. Experimentally, we observe a modulation depth of about 6 mV. This is to be compared with an expected signal of ~145 µV in the absence of heterodyne gain, and a detector rms noise of 1.1 mV at the detection bandwidth used (200 MHz).

It is sometimes assumed that reflection off a rough surface distorts the wave-front in such a way that when that signal is mixed with the flat wave-front of the reference arm, the interference averages out across the beam cross section, resulting in a significant decrease of the heterodyne modulation. However, we focus the sample and reference arm signals on the detector down to a spot size that is close to being diffraction limited. Since the phase front of the two interfering beams are approximately flat over distances similar to the size of a diffraction limited spot, almost no spatial averaging of the interference is expected. In contrast, the speckle manifests itself as a throughput modulation of the sample arm. In other words, the heterodyne gain can be preserved even in the presence of speckle, but a throughput modulation, seen as a modulation of the heterodyne envelope amplitude, can be observed as different spots on the target are probed. If the target is moved while different averages are acquired, the average trace obtained is expected to have half the amplitude for the heterodyne modulation, as seen in FIG. 8.

FIGS. 9A-9C illustrate the effect of pulse-to-pulse phase jitter by comparing the data obtained when the delay between sample and reference is fixed and when we vibrate the sample-arm reflector along the optical axis to introduce phase jitter in the heterodyne beat. By superposing the data from each pulse of a series of 2000 pulses, the underlying heterodyne modulation is blurred out, but the envelope is traced out. The vibration affects the phase of the heterodyne modulation for each pulse but the envelope is preserved, indicating that the heterodyne gain is preserved.

The quantity plotted in each of FIGS. 9A and 9B is:

$$s(t) = \frac{S_{Detector} - I_R(t)}{2\sqrt{I_R(t)}} = \sqrt{I_s(t)} \cos(\Delta f(t) \cdot t + \varphi)$$

where $S_{Detector}$ is the detector signal, $I_R$ is the intensity in the reference arm (local oscillator), $I_S$ is the intensity in the sample arm, and $\Delta f$ if the difference frequency between the reference and sample arms (heterodyne beat frequency).

Using the Hilbert transform we can obtain the analytic representation of the quantity plotted:

$$s_A(t) = s(t) + i\hat{s}(t) = s_M(t) e^{i(\theta(t)+\theta_0)}$$

where $\hat{s}(t)$ is the Hilbert transform of $s(t)$, $s_M(t)$ is the instantaneous amplitude (envelope), $\theta(t)$ is the instantaneous phase, $\theta_0$ is an average phase offset for pulse trains. This expression illustrates one possible method to extract the information carried by the heterodyne signal, in this case as the instantaneous amplitude and phase of the analytic representation.

Adding the effect of speckle and phase jitter to the analytical representation, we obtain:

$$S_{speckle} \cdot s_M(t) e^{i(\theta(t)+\theta_0+\theta_{jitter})}$$

where $s_M(t)$ is the instantaneous amplitude (envelope) carrying the spectral signature, $\theta(t)$ is the instantaneous phase carrying the spectral signature, $\theta_0$ is an average phase offset for pulse trains (does not contain spectral information), $S_{speckle}$ is a constant amplitude factor for each pulse (does not contain spectral information), $\theta_{jitter}$ is a constant for each pulse (does not contain spectral information).

$s_M(t)$ and $\theta(t)$ contain information about the absorption and dispersion along the sample-arm. $\theta_{jitter}$ is affected by vibrations, from pulse to pulse, i.e., variation of the time delay between the two arms (phase jitter). If the sample-arm reflector is rough, speckle can lead to throughput variations from pulse to pulse at the receiving telescope, due to the limited collection numerical aperture (NA). At the approximately 100 ns time scale of the pulse duration, speckle or phase variation is not expected to change the envelope phase and amplitude of each pulse and hence the spectral information is immune to such jitter or variations. In other words, $\theta_{jitter}$ and $S_{speckle}$ can be considered to be constant for a given pulse.

Chirp delay heterodyne measurements are time gated, with heterodyne information carried by each pulse. For example, a single 300 ns long pulse carries the coherently amplified signal. The instantaneous amplitude and/or phase can be retrieved from each single pulse. And then these quantities can be averaged over several pulses to increase SNR. In other words, we do not require coherence of the heterodyne beat across several pulses. Pulse-to-pulse phase jitter and speckle amplitude fluctuations are thus not concerns.

In FIG. 8, the dashed trace corresponds to the averaged instantaneous amplitude extracted from the analytic representation of the heterodyne signal obtained for each pulse. We make no assumption on the pulse-to-pulse phase relationship of the heterodyne signal to obtain this data. This envelope retrieval is thus robust against phase-jitter. Note also that this data is obtained using a rough target, which introduces speckle. Furthermore, the rough target is moved during acquisition, such that this data set corresponds to a situation with time-varying speckle and phase jitter. As can be seen, the heterodyne gain is preserved (albeit reduced by a factor of ~2 because of speckle averaging) in this challenging situation and the information (here heterodyne beat envelope) can be extracted on a pulse-to-pulse basis and then averaged.

The quality of the averaging process is illustrated in FIG. 10, which shows the Allan deviation of the gas absorption dip depth. The Allan deviation confirms that the measurements average well. This data set is obtained with sand-blasted aluminum as the moving target and with phase jitter introduced by vibrating the target along the optical axis. The total number of averages was limited here by the data acquisition hardware. Our ability to average information obtained independently from different pulses means we do not require coherence of the heterodyne beat from pulse to pulse. This assures that the technique is robust against vibrations.

From pulse to pulse, there may be phase jitter which will correspond to an arbitrary phase offset (approximately constant over the duration of one pulse) to the instantaneous phase. If a series of instantaneous phase vs time curves are acquired (one per pulse), the data can be pinned to the same starting value to correct for these offsets and obtain a relative phase variation across the duration of the pulse. Other methods could be more robust against noise, such as, for each pulse, searching for the value of the constant phase offset that reduces or minimizes the difference between the instantaneous phase data of this pulse and of that of the other pulses.

Phase and Dispersion Detection Using Chirp-Delay Spectroscopy

Dispersion spectroscopy is a technique that measures the dispersion (i.e., variation of refractive index with frequency) of a sample. In contrast with absorption spectroscopy, dispersion spectroscopy has the advantage that information is stored in the phase of the measured signal, rather than the amplitude, so the technique does not suffer from dynamic range issues (e.g., dynamic range compression due to a large background signal) or optical power fluctuations.

As explained above, we use the natural chirp of one or more single mode lasers (e.g., distributed feedback semiconductor lasers, QCLs, external cavity lasers using a diffraction grating or other frequency selective element, or other single-mode lasers) to produce a difference frequencies between two time-delayed channels (reference and signal):

$$P(t)_{CD,i} = P(t)_{ref,i} + P(t)_{s,i} + 2\sqrt{P(t)_{ref,i} \cdot P(t)_{s,i}} \cdot \cos\left[(\omega_{ref,i}(t) - \omega_{s,i}(t))t + (\varphi_{ref,i} - \varphi_{s,i}(t))\right]$$

where $P(t)_{CD,i}$ refers to the chip-delay instantaneous intensity detected for the $i^{th}$ laser pulse, $P(t)_{ref,i}$ is the instantaneous reference pulse intensity, $P(t)_{s,i}$ is the instantaneous signal pulse intensity, and $\varphi_{ref,i}$ and $\varphi_{s,i}(t)$ are the corresponding phases. For this case, the signal arm is tapped off the reference arm and has the same phase as the reference except for the influence of any dispersive material in the signal arm. The reference signal can be tapped off from the laser source output by an optical beam splitter. The rest of the laser light forms a signal pulse that interacts with a substance and is represented here as $P(t)_{s,i}$. The frequency shift between reference and signal pulses resulting from different optical lengths in the two channels is $\Delta\omega i(t) = [\omega_{ref,i}(t) - \omega_{s,i}(t)]$. This frequency difference is itself generally time dependent unless the chirp of the laser is linear. The chirp of the laser $\omega_{ref,i}(t)$ can be characterized a priori and can be assumed to be a known function for lasers, such as semiconductor distributed feedback lasers, repeatable from pulse to pulse and over time. The phase term $\Delta\varphi =$ ($\varphi_{ref,i}-\varphi_{s,i}(t)$) is dependent on the delay between arms, and the time-dependence of the signal phase $\varphi_{s,i}(t)$ is affected by any dispersive material in the signal arm.

Other mathematical formulations are possible. For instance, the dispersion in the signal arm can be wrapped into $\varphi_{s,i}(t)$. We choose to let $[\omega_{ref,i}(t)-\omega_{s,i}(t)]$ represent the effect of the laser chirp and the delay line, and $\omega_{s,i}(t)$ represent the effect of dispersion in the signal arm.

Information about the absorption and dispersion of the sample arm is contained in the "beating term" $2\sqrt{P(t)_{s,i}/P(t)_{ref,i}}\cdot\cos[(\omega_{ref,i}(t)-\omega_{s,i}(t))t+(\varphi_{ref,i}-\varphi_{s,i}(t))]$, which can be extracted from the measurement $P(t)_{CD,i}$ provided that one has also measured $P(t)_{ref,i}$ and $P(t)_{s,i}$, or if $P(t)_{s,i}$ is small enough to be neglected. A plot of $2\sqrt{P(t)_{s,i}/P(t)_{ref,i}}\cdot\cos[(\omega_{ref,i}(t)-\omega_{s,i}(t))t+(\varphi_{ref,i}-\varphi_{s,i}(t))]$ is shown in FIG. 7 for a particular experimental realization. The intensity envelope is extracted from the signal and shown in FIG. 11, indicating the absorption line. The instantaneous phase is also extracted and shown in FIG. 11, which is dominated by the rapidly varying term $\varphi_{s,i}(t)$ in the vicinity of the absorption line.

There are different ways to extract the envelope and phase of the signal. One can fit the signal to the expected functional form. Another method is to use an analytic representation of the signal. The analytic signal $s_A(t)$ of the measured signal $s(t)$ is the function $s_A(t)=s(t)+i\hat{s}(t)=s_M(t)e^{i\varphi(t)}\hat{s}(t)s(t)s_M(t)\varphi(t)$ By extracting the phase of the heterodyne modulation, one can measure the dispersion along the sample arm path (i.e., the difference between the integrated phase accumulated as light propagates along the sample arm and reference arms). In the presence of a gas with a narrow absorption line, an anomalous dispersion may be measured. The measurement of this dispersion is baseline free and can lead to quantification of the analyte without the need to normalize the data to the emitted pulse intensity, as is usually required for absorption measurements.

While heterodyne techniques as the one described here are typically used to amplify the signal, the technique described here is relevant even in the presence of similar intensities for the sample arm and the local oscillator, since it allows convenient measurement of the dispersion along the sample arm.

FIGS. 12A-12C show laser arrays that can be used as laser sources for chirp delay heterodyne spectroscopy, e.g., in place of the laser source 10 shown in FIGS. 2 and 6. The laser source 1201 is FIG. 12A includes an array of independent lasers 101, 102, . . . 103. These lasers can be actuated independently or in concert to form an array of laser beams, which are multiplexed into a single output beam by a laser beam combining module 104, using, for example, aperture combining, spectral beam combining, or coherent beam combining. FIG. 12B shows a laser source 1202 with an array of lasers 101, 102, . . . 103 fabricated on a single semiconductor chip 105. For instance, the array may be an array of quantum cascade lasers, each of which emits light at a different center wavelength. The laser source 1202 may be actuated independently or together to form an array of laser beams, which are multiplexed into a single output beam by a laser beam combining module 104, using, for example, aperture combining, spectral beam combining, or coherent beam combining. FIG. 12C shows a laser source 1203 that includes an array of lasers 101, 102, . . . 103 fabricated with the combining module 104 on the same semiconductor chip 106. Again, the lasers 101 . . . 103 emit an array of laser beams, which are multiplexed into a single output beam by the laser beam combining module 104.

FIGS. 13A and 13B show side and on-axis view of a lens and reflector assembly 1300 that be used in either (or both) reference or sample arms. The lens and reflector assembly 1300 include a lens or lens assembly 1301 that focuses an incoming beam 1300 is focused onto a reflector 1302. The reflector 1302 produces a reflection 103 that can be specular or diffused and is captured by the same lens 1301. The exiting beam 1304 is parallel to the incoming beam 1300 if the reflector 1302 is placed one focal length away from the lens 1301.

As shown in FIG. 13B, it may be desirable to have the two beams 1300 and 1304 be parallel but not coincident. In particular, this reduces or eliminates feedback into the laser by aperturing the return beam so that it is not directed back towards the laser, but instead is only allowed to recombine with the return beam from the other interferometer arm and propagate towards the detector. This can be achieved by using a lens 1301 with a diameter larger than the incident beam 1300. By properly choosing the angle of the reflector, it is possible to ensure that the reflected beam 1304 is fully captured by the lens 1301 and does not intersect the incident beam 1300. If the laser is apertured to allow feedback only from the aperture defined by the incident beam 1300, then little to no feedback is expected from beam 1304.

FIG. 14B shows an alternative chirp delay heterodyne system 1400. A laser source 1400 emits a collimated chirped pulse towards a beam splitter 1401, creating two portions of the chirped pulse: one portion propagates along a reference arm 1404, and the other portion propagates along a sample arm 1405. The two portions are recombined into a single beam using a second beam splitter 1407. The combined beam is then focused onto a detector 1406. Mirrors 1402 and 1403 in the reference and sample arms to guide the reference and signal pulses.

FIG. 15A shows a beam combiner 1502 that multiplexes a laser pulse 1500 from the reference arm and a laser pulse 1501 from the sample arm. In other words, the beam combiner 1502 overlaps both pulses into a single beam using, for example, a beam splitter. The resulting pulse 1503 features a heterodyne modulation that results from the interference of the two light pulses. If the sample arm pulse 1503' is strongly attenuated, as shown in FIG. 15B, coherent gain can be used to retrieve sample transmission information: the heterodyne modulation amplitude of the resulting pulse 1503' is $2\sqrt{I_S I_R}\gg I_S$, for $I_S\ll I_R$, where $I_S$ is the transmitted intensity in sample arm and $I_R$ is the transmitted intensity in the reference arm.

FIG. 16 illustrates chirp delay heterodyne spectroscopy with a train of N consecutive chirped pulses from N lasers emitting at respectively wavelength $\lambda 1, \lambda 2, \ldots \lambda N$. These pulses are split into chirped reference pulses 1600 and chirped sample samples 1601, which interrogate the sample, and are then combined with the chirped reference pulses 1600 into a single beam, for example, by a beam splitter 1602, resulting in the train of pulses 1603 featuring heterodyne modulations of different amplitudes for each pulse 1603. By extracting the instantaneous amplitude (or instantaneous phase) of each pulse 1603, the transmission of the sample arm at the wavelength corresponding to that pulse can be derived, in order to obtain a transmission spectrum 1604. Note that 'wavelength corresponding to a pulse' refers to the average wavelength of the chirped pulse, since the laser wavelength varies during each chirped pulse.

FIG. 17 illustrates chirp delay heterodyne spectroscopy with a train of N consecutive chirped pulses from one or more lasers (e.g., N lasers) emitting at the same wavelength (λ1). The chirped pulses are split into chirped reference pulses 1700 and chirped sample pulses 1701. The chirped sample pulses 1701 interrogate the same and are combined with the chirped reference pulses 1700 into a single beam, for example, by a beam splitter 1702, that includes a train of chirped pulses 1703 with heterodyne modulation. The chirped pulses 1703 can be averaged. The sample absorption and dispersion information carried by the heterodyne modulation can be extracted from the average pulses, or the sample absorption and dispersion information carried by the heterodyne modulation can be extracted first and then averaged.

FIG. 18 shows a train of chirped laser pulses 1800 emitted by a laser source and split into two copies by a beam splitter 1803. A first copy of the chirped pulses propagates along the reference arm, and the other propagates along the sample arm. Consider two consecutive pulses 1801 and 1802 on the reference arm, with their respective copies on the sample arm 1801' and 1802'. Further consider that the optical path difference between the two arms is such that the pulse 1802 arrives at a second beam splitter 1804 at the same time as pulse 1801', the signal-arm copy of pulse 1801. This situation can occur with large optical path differences between the sample and reference arms. Pulses 1802 and 1801' can still interfere and result in a pulse 1805 featuring a heterodyne modulation, e.g., a heterodyne beat or a homodyne beat if the delay between the two arms is a full integer number of the pulse period. While the heterodyne modulation of consecutive pulses may feature random phase offsets, these random phase offsets do not prevent the sample absorption and dispersion information carried by the heterodyne modulation from being extracted on a pulse-to-pulse basis and then averaged for increased signal-to-noise ratio.

FIG. 19A is a plot of measured laser emission wavenumber vs time for a pulsed distributed feedback quantum cascade laser. FIG. 19B shows the heterodyne modulation (beat frequency) produced when two copies of these pulses interfere on a detector, with various optical path difference between the two copies as indicated in the legend.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of making a spectroscopic measurement of a sample, the method comprising:
   generating a chirped signal pulse with a single-mode laser in response to an electrical pulse;
   illuminating the sample with the chirped signal pulse so as to cause the chirped signal pulse to interact with the sample;
   detecting a heterodyne modulation caused by interference of the chirped signal pulse and a chirped reference pulse generated with the single-mode laser, the heterodyne modulation depending on a dispersion and/or an absorption of the sample; and
   determining the dispersion and/or the absorption of the sample from the detected heterodyne modulation.

2. The method of claim 1, wherein the chirped signal pulse is chirped due to at least one of heating of the single-mode laser by the electrical pulse or a carrier density change of the single-mode laser by the electrical pulse.

3. The method of claim 1, wherein the single-mode laser is a distributed feedback (DFB) laser and generating the signal pulse comprises emitting a chirped optical pulse from the DFB laser having a pulse duration of about 10 nanoseconds to about 10 microseconds and a chirp rate ranging from about 0.2 wavenumbers per hundred nanoseconds to about 4 wavenumbers per hundred nanoseconds.

4. The method of claim 1, wherein generating the signal pulse comprises:
   emitting a chirped optical pulse from the single-mode laser in response to the electrical pulse; and
   splitting the chirped optical pulse into the chirped signal pulse and the chirped reference pulse.

5. The method of claim 1, wherein generating the chirped signal pulse comprises emitting the chirped signal pulse from the single-mode laser at a first time and the chirped reference pulse is emitted by the single-mode laser at a second time different than the first time.

6. The method of claim 1, further comprising:
   estimating the dispersion of the sample based on the instantaneous phase.

7. The method of claim 1, further comprising:
   estimating the absorption of the sample based on the instantaneous amplitude.

8. The method of claim 1, wherein the chirped signal pulse is a first chirped signal pulse, the electrical pulse is a first electrical pulse, the chirped reference pulse is a first chirped reference pulse, and the heterodyne modulation is a first heterodyne modulation, and further comprising:
   generating a second chirped signal pulse with the single-mode laser in response to the second electrical pulse;
   illuminating the sample with the second chirped signal pulse so as to cause the second chirped pulse to interact with the sample; and
   detecting a second heterodyne modulation caused by interference of the second chirped signal pulse and a second chirped reference pulse generated with the single-mode laser, the second heterodyne modulation depending on the dispersion and/or the absorption of the sample.

9. The method of claim 8, further comprising:
   averaging the first heterodyne modulation and the second heterodyne modulation.

10. The method of claim 8, further comprising:
    dithering a phase of the second chirped reference pulse with respect to a phase of the first chirped reference pulse.

11. The method of claim 8, wherein the instantaneous frequency is a first instantaneous frequency and further comprising:
    determining a second instantaneous phase of the second heterodyne modulation; and
    averaging the first instantaneous phase and the second instantaneous phase.

12. The method of claim 8, wherein the instantaneous amplitude is a first instantaneous amplitude and further comprising:
    determining a second instantaneous amplitude of the second heterodyne modulation; and
    averaging the first instantaneous amplitude and the second instantaneous amplitude.

13. A system for making a spectroscopic measurement of a sample, the system comprising:
    a single-mode laser, in optical communication with the sample, to generate a chirped signal pulse in response to an electrical pulse, the chirped signal pulse interacting with the sample; and
    a photodetector, in optical communication with the sample, to detect a heterodyne modulation caused by interference of the chirped signal pulse and a chirped reference pulse generated with the single-mode laser, the heterodyne modulation being related to a dispersion and/or an absorption of the sample.

14. The system of claim 13, wherein the chirped signal pulse is chirped due to at least one of heating of the single-mode laser by the electrical pulse or a carrier density change of the single-mode laser by the electrical pulse.

15. The system of claim 13, wherein the single-mode laser is a distributed feedback (DFB) laser and the chirped signal pulse has a pulse duration of about 10 nanoseconds to about 10 microseconds and a chirp rate ranging from about 0.2 wavenumbers per hundred nanoseconds to about 4 wavenumbers per hundred nanoseconds.

16. The system of claim 13, wherein the signal-mode laser is configured to generate the chirped signal pulse at a first time and the chirped reference pulse at a second time different than the first time.

17. The system of claim 13, further comprising:
    a beam splitter, in optical communication with the single-mode laser, to split a chirped optical pulse emitted by the single-mode laser into the chirped signal pulse and the chirped reference pulse.

18. The system of claim 13, further comprising:
    circuitry, operably coupled to the photodetector, to determine an instantaneous phase and/or an instantaneous amplitude of the beat frequency.

19. The system of claim 18, wherein the circuitry is further configured to estimate a dispersion of the sample based on the instantaneous phase.

20. The system of claim 18, wherein the circuitry is further configured to estimate an absorption of the sample based on the instantaneous amplitude.

21. The system of claim 18, wherein:
the chirped signal pulse is a first chirped signal pulse,
the electrical pulse is a first electrical pulse,
the chirped reference pulse is a first chirped reference pulse,
the heterodyne modulation is a first heterodyne modulation,
the single-mode laser is configured to generate a second chirped signal pulse with the single-mode laser in response to the second electrical pulse, the second chirped signal pulse interacting with the sample; and
the photodetector is configured to detect a second heterodyne modulation caused by interference of the second chirped signal pulse and a second chirped reference pulse generated with the single-mode laser, the second heterodyne modulation depending on the dispersion and/or absorption of the sample.

22. The system of claim 21, wherein the circuitry is configured to average the first heterodyne modulation and the second heterodyne modulation.

23. The system of claim 21, wherein:
the instantaneous phase is a first instantaneous phase, and
the circuitry is configured to determine a second instantaneous phase of the second heterodyne modulation and to average the first instantaneous phase and the second instantaneous phase.

24. The system of claim 21, wherein:
the instantaneous amplitude is a first instantaneous amplitude, and
the circuitry is configured to determine a second instantaneous amplitude of the second heterodyne modulation and to average the first instantaneous amplitude and the second instantaneous amplitude.

* * * * *